US011704791B2

(12) United States Patent
Yang et al.

(10) Patent No.: US 11,704,791 B2
(45) Date of Patent: Jul. 18, 2023

(54) MULTIVARIATE AND MULTI-RESOLUTION RETINAL IMAGE ANOMALY DETECTION SYSTEM

(71) Applicant: Topcon Corporation, Tokyo (JP)

(72) Inventors: Qi Yang, Foster City, CA (US); Bisrat Zerihun, Santa Clara, CA (US); Charles A. Reisman, Mamaroneck, NY (US)

(73) Assignee: TOPCON CORPORATION, Tokyo (JP)

( * ) Notice: Subject to any disclaimer, the term of this patent is extended or adjusted under 35 U.S.C. 154(b) by 878 days.

(21) Appl. No.: 16/552,467

(22) Filed: Aug. 27, 2019

(65) Prior Publication Data

US 2020/0074622 A1    Mar. 5, 2020

Related U.S. Application Data

(60) Provisional application No. 62/724,864, filed on Aug. 30, 2018.

(51) Int. Cl.
| | |
|---|---|
| *G06K 9/00* | (2022.01) |
| *A61B 3/02* | (2006.01) |
| *G06T 7/00* | (2017.01) |
| *G06N 3/08* | (2023.01) |
| *A61B 3/10* | (2006.01) |

(Continued)

(52) U.S. Cl.
CPC .......... *G06T 7/0012* (2013.01); *A61B 3/102* (2013.01); *G06N 3/08* (2013.01); *G06N 20/20* (2019.01); *A61B 3/12* (2013.01); *A61B 5/7275* (2013.01); *G06N 3/045* (2023.01); *G06T 2207/30041* (2013.01)

(58) Field of Classification Search
CPC ............. G06K 9/00; G16H 30/20; A61B 3/02
USPC ....... 382/100, 103, 106, 130–133, 140, 156, 382/162, 168, 173, 181, 199, 209, 219, 382/254, 260, 274, 285, 294, 312; 378/4, 378/21; 351/205, 237
See application file for complete search history.

(56) References Cited

U.S. PATENT DOCUMENTS

| | | | |
|---|---|---|---|
| 10,468,142 B1* | 11/2019 | Abou Shousha | G16H 30/20 |
| 2015/0110372 A1* | 4/2015 | Solanki | G16H 50/20 |
| | | | 382/130 |

(Continued)

OTHER PUBLICATIONS

Extended European Search Report for European Patent Application No. 19194538.5 dated Jan. 29, 2020.

(Continued)

*Primary Examiner* — Seyed H Azarian
(74) *Attorney, Agent, or Firm* — Pearne & Gordon LLP

(57) ABSTRACT

Machine learning technologies are used to identify and separating abnormal and normal subjects and identifying possible disease types with images (e.g., optical coherence tomography (OCT) images of the eye), where the machine learning technologies are trained with only normative data. In one example, a feature or a physiological structure of an image is extracted, and the image is classified based on the extracted feature. In another example, a region of the image is masked and then reconstructed, and a similarity is determined between the reconstructed region and the original region of the image. A label (indicating an abnormality) and a score (indicating a severity) can be determined based on the classification and/or the similarity.

22 Claims, 12 Drawing Sheets

(51) Int. Cl.
*G06N 20/20* (2019.01)
*A61B 5/00* (2006.01)
*A61B 3/12* (2006.01)
*G06N 3/045* (2023.01)

(56) References Cited

U.S. PATENT DOCUMENTS

| | | | | |
|---|---|---|---|---|
| 2017/0357879 | A1* | 12/2017 | Odaibo | G06F 18/254 |
| 2018/0214087 | A1* | 8/2018 | Balaji | G06V 10/454 |
| 2019/0038249 | A1* | 2/2019 | Itu | G16H 20/00 |
| 2020/0020098 | A1* | 1/2020 | Odry | G06V 10/7715 |

OTHER PUBLICATIONS

Pimentel, et al., "A Review of Novelty Detection", Signal Processing, vol. 99, pp. 215-249, 2014.
Ioffe, et al., "Batch Normalization: Accelerating Deep Network Training by Reducing Internal Covariate Shift", arXiv preprint arXiv:1502.03167, pp. 1-11, 2015.
Kingma, et al., "ADAM: A Method for Stochastic Optimization", ICLR, arXiv preprint arXiv:1412.6980, pp. 1-15, 2015.
Sidibé, et al., "An anomaly detection approach for the identification of DME patients using spectral domain optical coherence tomography images", Computer Methods and Programs in Biomedicine, pp. 1-27, Sep. 2, 2016.
Haselmann, et al., "Anomaly Detection using Deep Learning based Image Completion", IEEE, 17th International Conference on Machine Learning and Applications (ICMLA), pp. 1237-1242, Nov. 16, 2018.
Chalapathy, et al., "Anomaly Detection Using One-Class Neural Networks", arXiv preprint arXiv:1802.06360, pp. 1-13, Jan. 14, 2019.
Denton, et al., "Deep Generative Image Models using a Laplacian Pyramid of Adversarial Networks", In Advances in neural information processing systems, pp. 1-10, Jun. 18, 2015.
Chalapathy, et al., "Deep Learning for Anomaly Detection: A Survey", arXiv preprint arXiv:1901.03407, pp. 1-50, Jan. 24, 2019.
Schlachter, et al., "Deep One-Class Classification Using Intra-Class Splitting", Institute of Signal Processing and System Theory, University of Stuttgart, Germany, pp. 1-5, Sep. 16, 2019.
He, et al., "Deep Residual Learning for Image Recognition", In Proceedings of the IEEE conference on computer vision and pattern recognition, pp. 1-12, Dec. 10, 2015.
Clevert, et al., "Fast and Accurate Deep Network Learning by Ex[onential Linear Units (ELUs)", arXiv preprint arXiv:1511.07289, pp. 1-14, Feb. 22, 2016.
Long, et al., "Fully Convolutional Networks for Semantic Segmentation", In Proceedings of the IEEE conference on computer vision and pattern recognition, pp. 1-10, Mar. 8, 2015.
Erfani, et al., "High-dimensional and large-scale anomaly detection using a linear one-class SVM with deep learning", Pattern Recognition, vol. 58, pp. 121-134, Mar. 28, 2016.
Seeböck, et al., "Identifying and Categorizing Anomalies in Retinal Imaging Data", 29th Conference on Neural Infomnation Processing System (NIPS), pp. 1-5, Dec. 2, 2016.
Sermanet, et al., "OverFeat: Integrated Recognition, Localization and Detection using Convolutional Networks", arXiv preprint arXiv:1312.6229v4, pp. 1-16, Feb. 24, 2014.
Perera, et al., "Learning Deep Features for One-Class Classification", IEEE Transactions on Image Processing, vol. 28, No. 11, pp. 1-15, May 16, 2019.
Oza, et al., "One-Class Convolutional Neural Network", IEEE Signal Processing Letters, vol. 26, No. 2, pp. 1-5, Jan. 24, 2019.
Hariharan, et al., "Simultaneous Detection and Segmentation", In European Conference on Computer Vision, srXiv:1407.1808v1, pp. 1-16, Jul. 7, 2014.
Anantrasirichai, et al., "SVM-based texture classification in optical coherence tomography", IEEE 10th International Symposium on Biomedical Imaging, pp. 1-5, Jun. 28, 2014.
Schlegl, et al., "Unsupervised Anomaly Detection with Generative Adversarial Networks to Guide Marker Discovery", In International conference on information processing in medical imaging, arXiv:1703.05921v1, pp. 1-12, Mar. 17, 2017.
Simonyan, et al., "Very Deep Convolutional Networks for Large-Scale Image Recognition", ICLR, arXiv:1409.1556V6, pp. 1-14, Apr. 10, 2015.
Zeiler, et al., "Visualizing and Understanding Convolutional Networks", In European conference on computer vision, arXiv:1311.2901v3, pp. 1-11, Nov. 28, 2013.
Ravenscroft, et al., "Learning Feature Extractors for AMD Classification in OCT Using Convolutional Neural Networks", 2017 25th European Signal Processing Conference (EUSIPCO), pp. 51-55, Aug. 28, 2017.
Yu, et al., "Generative Image Inpaiting with Contextual Attention", In Proceedings of the IEEE conference on computer vision and pattern recognition, arXiv:1801.07892v2, pp. 1-15, Mar. 21, 2018.
Iizuka, S., Simo-Serra, E. and Ishikawa, H., 2017. Globally and locally consistent image completion. ACM Transactions on Graphics (ToG), 36(4), Article 107, pp. 1-14.
Y. LeCun, L. Bottou, Y. Bengio, and P. Haffner. Gradient-based learning applied to document recognition, Proceedings of the IEEE 86(11):2278-2324, Nov. 1998.

* cited by examiner

MULTIVARIATE AND MULTI-RESOLUTION RETINAL IMAGE ANOMALY DETECTION SYSTEM

CROSS-REFERENCE TO RELATED APPLICATIONS

This application claims priority to U.S. Provisional Application Ser. No. 62/724,864, filed on Aug. 30, 2018, entitled "MULTIVARIATE AND MULTI-RESOLUTION RETINAL IMAGE ANOMALY DETECTION SYSTEM", the entirety of which is incorporated herein by reference.

BACKGROUND OF THE INVENTION

Initial steps in medical diagnosis and treatment include identifying and separating abnormal and normal subjects before referring them to specialists, and identifying a possible disease type and treatment plan or otherwise indicate abnormal scans for further analysis by the specialist. Various computer-based systems currently exist for automating the above identifications. But these each suffer from deficiencies.

For example, various binary classifiers in machine learning systems distinguish one major disease from normalcy. But such classifiers often give unreliable responses to non-target class disease data—that is, inputs including diseases other than those the classifier is trained to detect. Further, because some non-major disease data is rare, it can be difficult to find a sufficient amount of data to train the classifiers. Still further, different eye diseases can carry different types of structural and functional changes to normalcy. Thus, two or more eye diseases may co-exist in one eye. In such cases, it is difficult to accurately identify the disease types without a significantly large amount of disease training data.

Additionally, anomaly detection systems can screen abnormal eyes using normative eye data (data from normal eyes) only as the training data or as a reference—that is, by identifying eye data as abnormal if it does not match the normative data used as a reference or for training. This processes mimics how doctors can intuitively tell if any eye is normal or abnormal. As a pre-screening step, these systems can remind doctors to look into data if the data is screened as abnormal (so all data with abnormal structural changes will be screened out), while systems with multiple binary classifiers only work for the disease categories they have been specifically trained for.

BRIEF SUMMARY OF THE INVENTION

According to one example of the disclosure herein, an image processing method comprises receiving a first image of an object; extracting, with a trained machine learning system, a feature of the first image or of a physiological structure shown in the first image, the first image being an input to the trained machine learning system; classifying, with a first trained classifier, the first image based on the extracted feature, the extracted feature being an input to the first trained classifier; and determining a label and/or score of the first image based on the classification.

In various embodiments of the above example, the method further comprises receiving a second image of the object; extracting, with the trained machine learning system, a feature of the second image or of a physiological structure shown in the second image, the second image being an input to the trained machine learning system; classifying, with a second trained classifier, the second image based on the extracted feature of the second image, the extracted feature of the second image being an input to the second trained classifier; and determining a label and/or score of the second image based on the classification; the first image and the second image are patches from a common cross-sectional image of the object; the first trained classifier is trained with normative images corresponding to a region of the first image that includes the extracted feature of the first image, and the second trained classifier is trained with normative images corresponding to a region of the second image that includes the extracted feature of the second image; the first image and the second image comprise at least some of the same data; the first image and the second image are from a common 3D volume; the first image and the second image do not comprise any of the same data; the first image and the second image have a different size or a different resolution; the first image and the second image are from different 3D volumes; the method further comprises determining a composite label or a composite score based on the label or the score of the first image and based on the label or the score of the second image; the method further comprises determining a composite label by comparing scores of a first predetermined number of images, to a predetermined threshold; and determining a composite score by performing a statistical calculation on a second predetermined number of images, wherein the first predetermined number of images includes at least the first image and the second image, and the second predetermined number of images includes at least the first image and the second image; the composite label represents an abnormality when a first set of consecutive images of the first predetermined number of images have a score less than a threshold, and the composite score is a minimum score of a second set of consecutive images of the second predetermined number of images; the method further comprises; determining an average of the score of the first image and the second image; the first image is a B-scan or a cross-sectional image that includes a depth dimension; the first image is an optical coherence tomography image; the label identifies whether the object is normal or abnormal, and the score indicates a degree of the normality or abnormality, or indicates a type of the abnormality; the first trained classifier is a binary classifier; the first trained classifier is a deep learning model; the first trained classifier is trained with only normative data; the first trained classifier is a one-class support vector machine; the trained machine learning system is a convolutional neural network; the object is an ophthalmological structure; and/or the first image is one of a plurality of patches, each of the plurality of patches being from a distinct spatial region of a common cross-sectional image of the object, and the first trained classifier is trained with training image patches from at least two of the distinct spatial regions.

According to second example, an image processing method comprises receiving a first image of an object; masking a region of the first image; reconstructing, with a first trained machine learning system, the region of the first image; determining a similarity between the reconstructed region of the first image and a corresponding region of the first image as received; and determining a label and/or score of the first image based on the determined similarity.

In various embodiments of the second example, the method further comprises receiving a second image of the object; masking a region of the second image; reconstructing, with a second trained machine learning system, the region of the second image; determining a similarity between the reconstructed region of the second image and a corresponding region of the second image as received; and determining a label and/or score of the second image based on the determined similarity; the first image and the second image are patches from a common cross-sectional image of the object; the first trained machine learning system is trained with normative images corresponding to the region of the first image, and the second trained machine learning system is trained with normative images corresponding to the region of the second image; the first image and the second image comprise at least some of the same data; the first image and the second image are from a common 3D volume; the first image and the second image do not comprise any of the same data; the first image and the second image have a different size or a different resolution; the first image and the second image are from different 3D volumes; the method further comprises determining a composite label or a composite score based on the label or the score of the first image and based on the label or the score of the second image; the method further comprises determining a composite label by comparing scores of a first predetermined number of images, to a predetermined threshold; and determining a composite score by performing a statistical calculation on a second predetermined number of images, wherein the first predetermined number of images includes at least the first image and the second image, and the second predetermined number of images includes at least the first image and the second image; the composite label represents an abnormality when a first set of consecutive images of the first predetermined number of images have a score less than a threshold, and the composite score is a minimum score of a second set of consecutive images of the second predetermined number of images; the method further comprises determining an average of the score of the first image and the second image; the first image is a B-scan or a cross-sectional image that includes a depth dimension; the first image is an optical coherence tomography image; wherein the label identifies whether the object is normal or abnormal, and the score indicates a degree of the normality or abnormality, or indicates a type of the abnormality; the first trained machine learning system is trained with only normative data; the object is an ophthalmological structure; the region of the first image corresponds to a retinal layer; the first trained machine learning system is a deep convolutional generative adversarial network; and/or the similarity is determined by a multi-scale similarity measure (MS-SSIM).

According to a third example, an image processing method comprises receiving a first image of an object; extracting, with a first trained machine learning system, a feature of the first image or of a physiological structure shown in the first image, the first image being an input the first trained machine learning system; classifying, with a first trained classifier, the first image based on the extracted feature, the extracted feature being an input to the first trained classifier; masking a region of the first image; reconstructing, with a second trained machine learning system, the region of the first image; determining a similarity between the reconstructed region of the first image and a corresponding region of the first image as received; and determining a label and/or score of the first image based on the classification and the determined similarity. As the third example is a combination of the first and second examples above, various embodiments thereof may include any of the above-described features relating to the first and second examples.

DETAILED DESCRIPTION OF THE INVENTION

Figure 1:
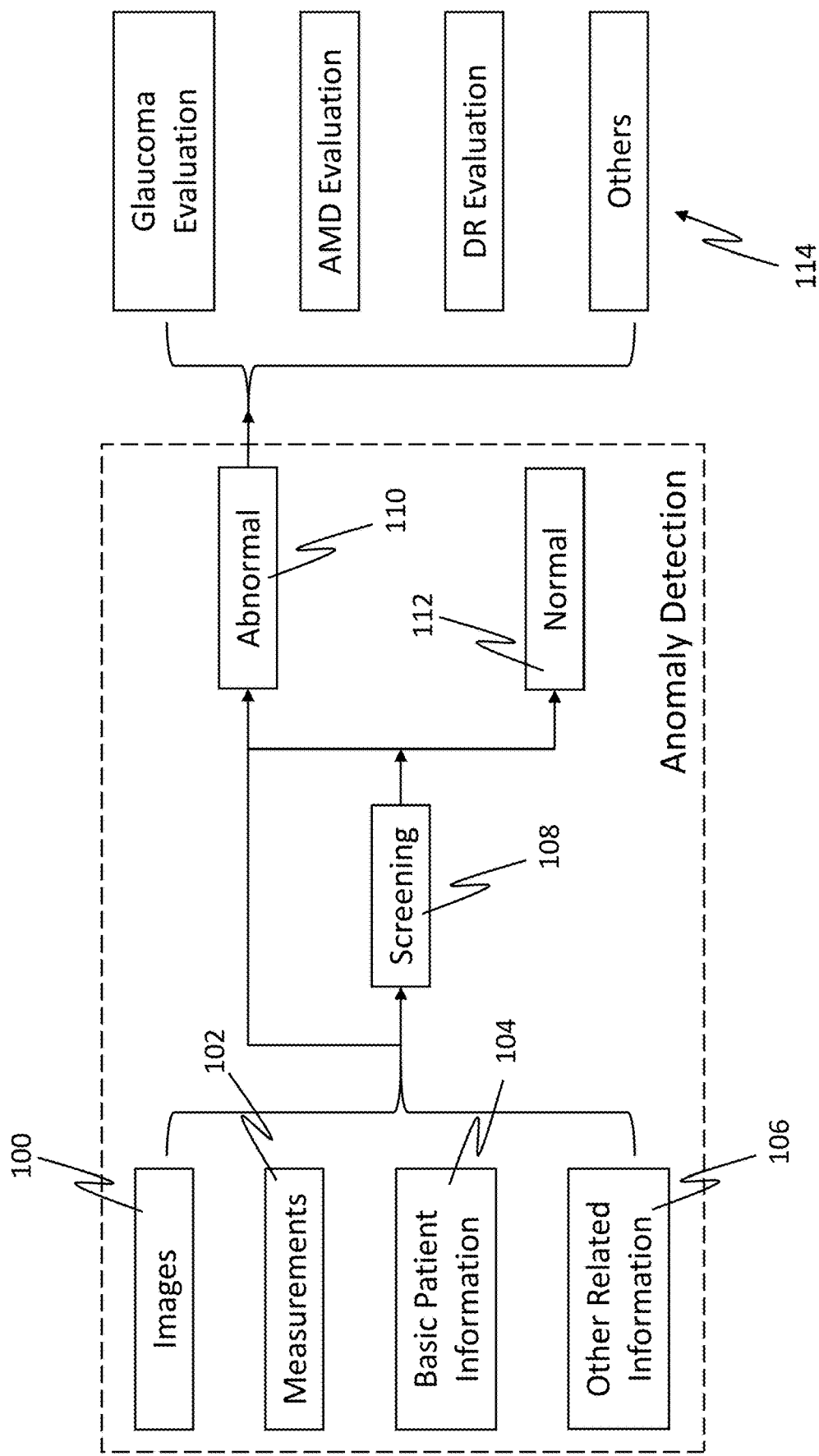
FIG. 1 illustrates an example system and method architecture of the present disclosure.

Because normative data (also referred to herein as normal data) is far more readily available than pathological data, it is easier to train anomaly detection system networks with large amounts of normative data. Further, pathological data collections can be strongly influenced and/or biased by specific inclusion/exclusion criteria in study protocols, whereas healthy/normal data collections may be less biased. Such training and testing can be performed using reference/normative database data sets or data sets typical of high-volume optometry clinics and/or other screening locations (primary care, chain pharmacies, etc.).

In view of the above, the present disclosure is directed to identifying and separating abnormal (used interchangeably with 'disease' herein) and normal subjects and identifying possible disease types with images (e.g., optical coherence tomography (OCT) images of the eye) based on machine learning technologies. These machine learning technologies can include, for example, convolutional neural networks (CNN) and support vector machines (SVMs) where the training data can include only normative data. For ophthalmologic applications, such diseases may include various retinal pathologies including glaucoma (where severity is often defined by Mean Deviation (MD) score from visual field tests); diabetic retinopathy (DR), and age-related macular degeneration (AMD) (which includes several stages including early (small drusen), intermediate (medium-sized drusen), and late (either or both wet and dry atrophic AMD)). Additional conditions may also include but are not limited to Retinitis pigmentosa (RP), uveitis, ischemias, other retinopathies, and choroidal pathologies.

As suggested above, other image analysis systems focus on fundus images or en face OCT images (with a camera-like X/Y planar view), which requires a large number of volumes/eyes to train because only a single image (or a small number of images) exist per volume/eye. In contrast, the present disclosure describes the ability to use B-scan (taken in the X/Z or Y/Z plane, the Z dimension representing depth) or derived scan views and cross-sectional analysis of 3D scans. 3D scans often have between 128 and 512 (even 1024 or more) B-scans (images) per volume, whereas enface-based analysis will often reduce a volume down to one or a small number of images thereby losing much of the available information. Thus, by preserving and utilizing multi-dimensional image data, more training data can be obtained from one eye and of rare diseases for which there is relatively less data. Further, analysis of B-scan or other feature abundant 2D images more closely corresponds with how retinal specialists traditionally have viewed 3D OCT volumes for pathologies.

By using these images/volumes, the systems and methods described herein can recognize structural changes occurring in various forms. For example, the input to a CNN can be B-scan views (full B-scans or smaller sections) where AMD structural changes are seen clearly, or the input can be thickness maps where for example glaucoma detection can be more easily seen with Retinal Nerve Fiber layer (RNFL) thickness maps. In other embodiments, the input can be texture information. A multiresolution system is also described that can accommodate structural changes occurring locally or globally.

As shown in FIG. 1, the architecture of the system described herein takes images of a patient's eye 100, measurements 102, patient information 104, and/or other related information 106 as inputs to a screener 108. The screener 108 then outputs an identification that the input information is either abnormal 110 or normal 112. When abnormal 110, the system further identifies and outputs the type of abnormality 114 (e.g., diseases such as glaucoma, AMD, diabetic retinopathy, and the like). Here it is noted that, in the case of ophthalmological screening, the input images 100 can be any retinal images, such as OCT or fundus images, or multi-modality images; the measurements 102 may include those taken or derived from the images, for example, thickness, blood flow measurements or other related measurement such as visual acuity, and intraocular pressure (IOP; which may associated with glaucoma); and the patient and related information 104, 106 may include, for example, age, gender, alcohol or drug use, and the like. The screening output identifications 110, 112 may be made at a B-scan level and/or volume level.

The above system can be implemented by one or more computers including one or more processors and associated memory. The input images 100 and information 102, 104, 106 may be provided by an input/output interface device. Particularly, the images may be input directly by an imaging system (such as an OCT imaging system), provided over a network, provided via a transferable memory medium, or the like. In some embodiments the above system may be implemented as part of the imaging system itself. Similarly, the outputs may be provided on an attached or networked display device, stored in memory, or printed on a tangible medium.

Figure 2:
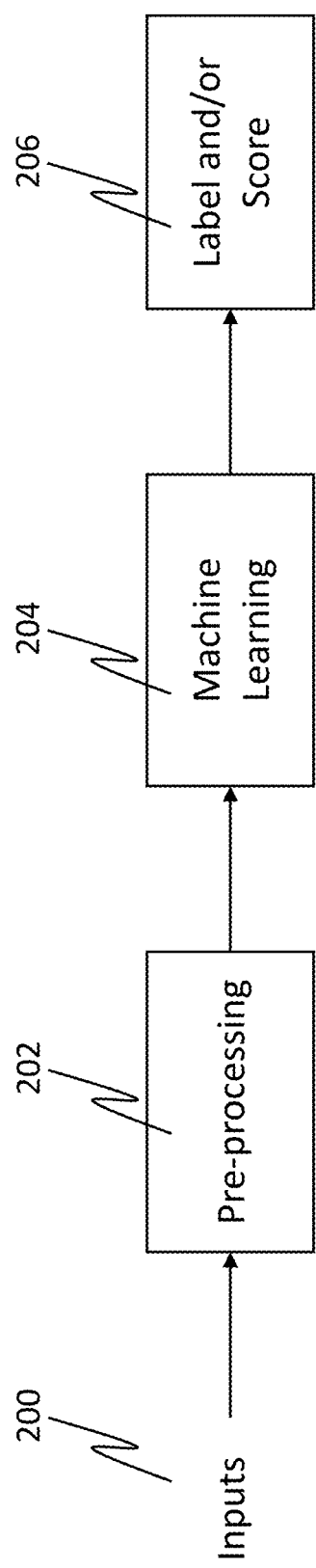
FIG. 2 illustrates an example architecture of an anomaly detection screener system and method of the present disclosure.

FIG. 2 illustrates an example architecture of an anomaly detection screener 108 system and method of the present disclosure. Therein, as noted above, the inputs 200 can be OCT B-scans (e.g., cross-sectional images including a depth dimension) and/or measurement maps/grids and/or other processed endpoints such as a multi-resolution OCTA signal. Further, the inputs 200 can be from any imaging or scan type, for example OCT scans. The inputs 200 may also be of any object, although the present disclosure refers to retinal and other ophthalmologic images. For example, the inputs 200 may be 6 mm×6 mm macular scans centered at fovea, 6 mm×6 mm disc scans centered at disc center scans, 12 mm×9 mm wide scans covering fovea and disc center, derived circle scans with different degrees of radii and/or types of eccentricity centered at disc center, derived oval scans with different degrees of radii and/or types of eccentricity centered at fovea, and the like. The anomaly detection process can also be extended to a partial or full 3D volume as well.

The input images 200 may first be pre-processed 202. The pre-processing 202 can include different forms of processing such as image flattening by internal limiting membrane (ILM) or other boundaries, image/map smoothing and speckle noise removal with Gaussian, Bilateral or other similar filters, image/map intensity normalization, thickness ratios, breaking the input images 200 into image patches (portions of an image, e.g., an extracted or cropped section of an image such as a cross-sectional B-scan), image resizing, and the like. When image patches are used, one input image or volume can optionally be broken down or segmented into multiple overlapping or non-overlapping sections by, for example, segmenting the images, extracting the sections, cropping the images, or the like. Each section would then constitute an image patch that can be processed further. In this manner, each full input image 200 can effectively provide multiple images for anomaly detection with each section. Pre-processing 202 can also include data augmentation by image shifting, flipping, intensity enhancement and other augmentation methods.

Depending on the embodiment, image patches may have different sizes, resolutions, be of different types (e.g., cross-sections or projection images from different planes if taken from a volume), be from different spatial locations, and the like. Put another way, the patches may be the result of any pre-processing performed on a larger image or volume. Where image patches are from distinct spatial locations, they would not have any of the same data; however, in some embodiments patches may be spatially overlapping and thus include common data. In other embodiments.

Following pre-processing 202, the processed image inputs are fed to a machine learning system 204 (e.g., a deep learning-based model) for processing. The machine learning based model may be deep CNN or deep Convolutional Generative Adversarial Network (DCGAN). Briefly, CNNs and DCGANs comprise multiple convolutional layers that each may include multiple filters. These filters are convolved with input data, such as the pre-processed input images, to extract relevant features. In some embodiments, the filters are configured to look at small patches (e.g., corresponding to the size of the filter) of the image input to the machine learning system, and calculate an activation value for a pixel corresponding to the patch (e.g., a center pixel of the patch). An activation map may then be developed by applying the filter across the entire image input to the machine learning system. By applying a series of convolutional layers, edges, parts, and models of the image input to the machine learning system can be extracted. Specific parameters for the filters of the machine learning system are determined via training with the training data. A complete CNN or DCGAN model includes, but is not limited to, convolution layers (e.g., for feature extracting purposes), pooling layers (e.g., to reduce dimensionality and/or to regularize the learning process to avoid overfitting during training), Batch Normalization (for faster convergence and regularization), activation layers (e.g., to introduce non linearity in to the system), un-pooling/Transposed convolution layers (e.g., to upscale feature maps in DCGAN) and fully connected layers (e.g., for classification/decision making purpose in CNN models). As detailed in the following examples, the machine learning system of the present disclosure may detect anomalies based on a classification technique and/or an image inpainting/reconstruction technique. When both techniques are used together, it is referred herein to as an ensemble anomaly detection technique.

Figure 3:
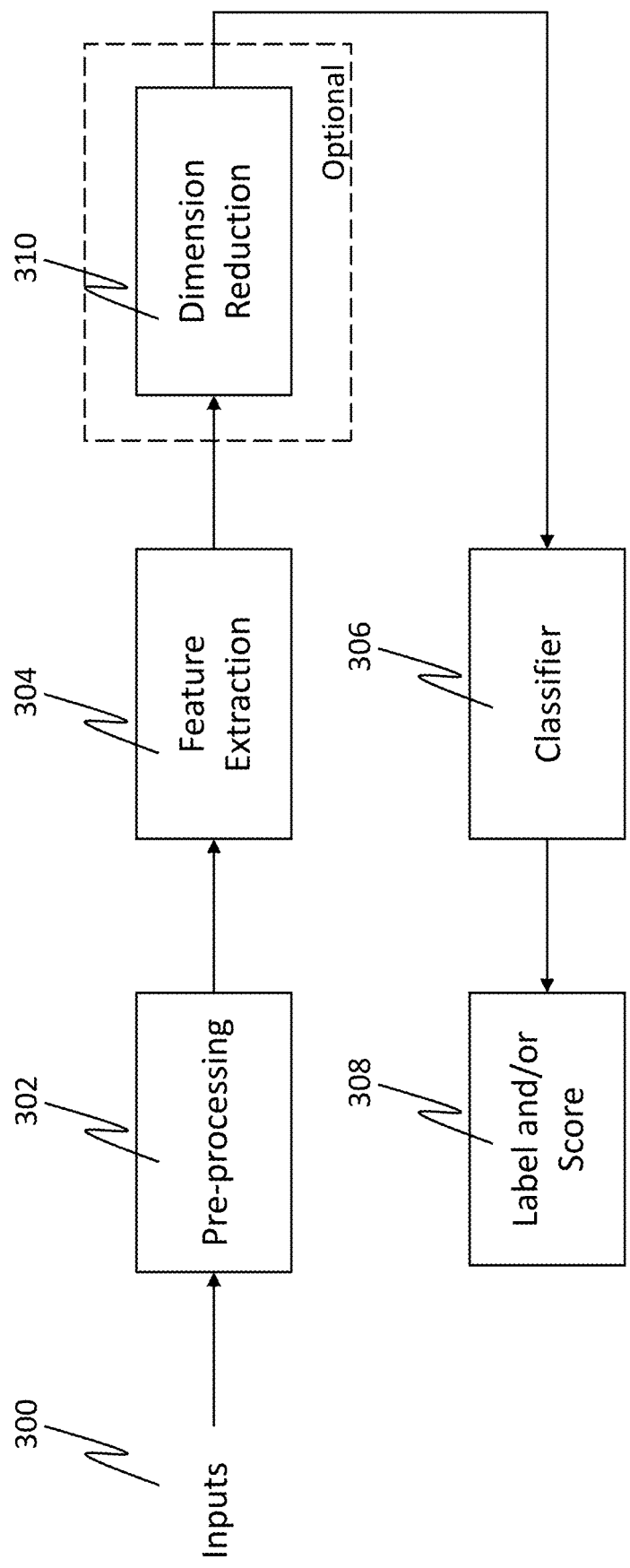
FIG. 3 illustrates an example classification architecture of an anomaly detection screener system and method of the present disclosure.

An example of the first approach, classification, is illustrated in FIG. 3. Compared with traditional techniques, that illustrated in FIG. 3 further includes a feature extraction machine learning system whereby the extracted features, rather than raw images, are input to a classifier. Accordingly, the classifier can be trained only with normative data. More particularly, as discussed above, input images 300 may first be pre-processed 302. Following pre-processing 302, features are extracted 304 from the input images 300 based on deep learning models, such as a pre-trained deep learning model (e.g., by using transfer learning) or deep learning models trained from scratch. Transfer learning allows for reuse of a pre-trained model for different tasks, or for using a pre-trained model as a starting point for a new task. Pre-trained models may include CNN models, for example VGG, Inception Network models (including Inception V3), ResNet, AlexNet, and others known to those of ordinary skill in the art. The features extracted are dependent on how the feature extraction machine learning system 304 is trained, but may relate to image brightness, edge features, colors, shapes, geographic/physiological regions, and the like. These features are preferably ones that are indicative of an abnormality.

The extracted features are then input to a classifier 306 (e.g., a one-class classifier or a binary classifier), which is trained to identify 'outliers' from the normative data used to train the classifier 306. In other words, features that do not appear to be normal (relative to corresponding features from the normative training data) may be identified by the classifier 306 as abnormal; and thus the image (or volume) from which the features were extracted, may be considered abnormal. For embodiments where an image is broken into multiple patches, each patch being input to the feature extraction system 304, the outputs thereof may be supplied to multiple classifiers 306, which in some embodiments can be ensembled. Ensemble classifiers operate in parallel and produce an output based on the outputs of each of the component classifiers within the ensemble. For example, the output of an ensemble classifier may be an average of the classifiers making up the ensemble.

In one embodiment, if four patches are taken from an input image, there may be two classifier models 306 each trained to process features extracted from two of the patches. Each of these two classifier models 306 may itself be an ensemble classifier, with component classifiers trained for each of the two patches input to the ensemble. Put another way, each classifier model 306 may be trained with images from one or more distinct spatial locations (each corresponding to a different patch). In this way, classification accommodates spatial variance of features in the training data set because different classifiers can be specifically trained for certain spatial locations. In other embodiments, such training and mapping of patches to classifiers 306 may be based on a type, number, location, size, and/or resolution of the patches. In other words, the classifiers 306 may each be trained with data corresponding to a particular patch(es) (e.g., its type, location, size, resolution, and the like). Therefore, particular patches may be mapped to particular classifiers and these particular classifiers ensembled to classify the input image.

The classifier 306 may be trained by normal samples only. In other words, the classifier 306 may be trained with data/images from only normal eyes (representing only normative data). The classifier 306 may be of any type, such as a one-class classifier in the form of a one-class support vector machine (SVM), one-class random forest model, or the like. In other embodiments, the classifier 306 may be a binary classifier. As shown in the example of FIG. 3, where the classifier 306 is a one-class classifier, the output 308 of the one-class classifier 306 is a label and a score of the processed images. The label indicates, for example, "normal" or "abnormal"; and the score indicates a degree or level of that label indication. The sign of the score may also indicate whether the label is normal/abnormal (e.g., negative: abnormal; positive: normal). The output may also include heat maps to indicate which part of the input images contribute (and how much) to the output label and/or score. Where a binary classifier is used, only a label would be output 308.

Depending on the score, a particular abnormality or disease may then be identified. For example, as discussed in further detail below with respect to FIGS. 9A and 9B, AMD is associated with scores of greater magnitude than drusen. Accordingly, a further analysis of the label and/or score output by the classifier 306 may be performed to identify the particular abnormality, for example, by comparing the scores with abnormal labels to thresholds (e.g., upper and lower bounds) associated with different abnormalities. These thresholds may be generated through a statistical calculation based on a test data set. In one embodiment, a receiver operating characteristic (ROC) curve may be utilized to identify thresholds that provide acceptable true-positive and false-positive rates for a desired application. In other examples, the threshold may be manually identified by a clinician based on a desired application.

Optionally, a dimension reduction step 310 may be performed on the extracted features prior to their input to the classifier 306. The dimension reduction may be principal component analysis (PCA), independent component analysis (ICA), or the like.

Figure 4:
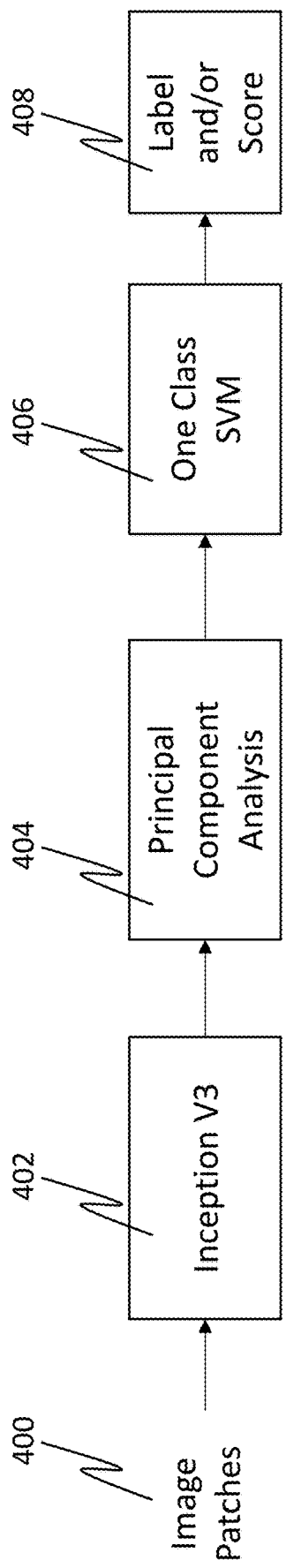
FIG. 4 illustrates another example classification architecture of an anomaly detection screener system and method of the present disclosure.

A particular non-limiting embodiment of the classification approach is illustrated in FIG. 4. Therein, image patches 400 (e.g., those obtained from pre-processing) are input to an Inception V3 deep learning model 402 for feature extraction. The features extracted by the Inception V3 model 402. The extract features are then subject to a PCA analysis 404 as part of the optional dimension reduction step. The PCA analyzed extract features are then input to a one-class SVM 406, which outputs the final label and/or score 408.

Figure 5:
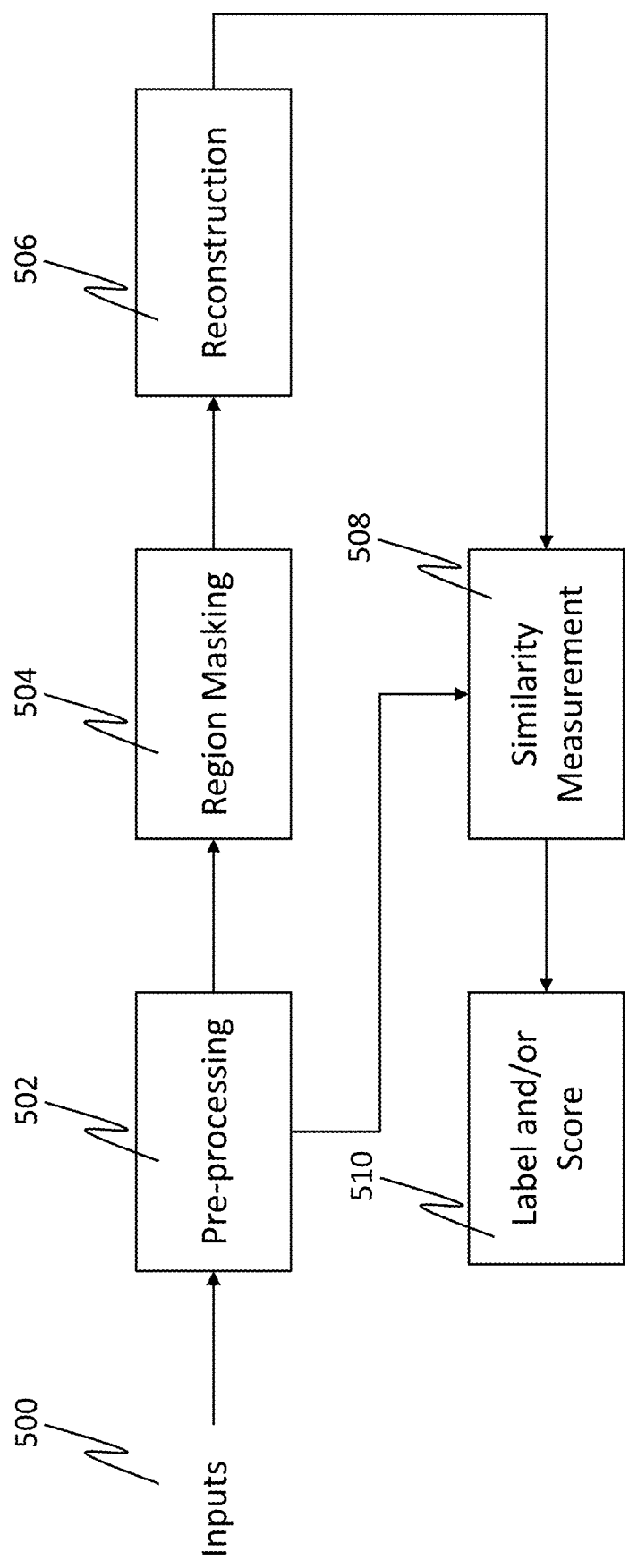
FIG. 5 illustrates an example image inpainting architecture of an anomaly detection screener system and method of the present disclosure.

An example of the second approach, image inpainting (a process of reconstructing portions of an image), is illustrated in FIG. 5. As discussed above with respect to FIGS. 3 and 4, input images 500 may first be pre-processed 502. This pre-processing 502 may be of any of the types of pre-processing already discussed. Regions of the pre-processed inputs are then masked 504, and those masked regions reconstructed (inpainted) 506 by a machine learning system.

Any region of the image may be randomly masked, for example, any structural region of the eye within the image including retinal layers (e.g., RNFL, Inner Plexiform layer (IPL), Retinal Pigment layer (RPE) and other layers). According to one embodiment, a sliding window is used to mask part of the input image or pre-processed image 500, 502. The window may take any size or shape, for example, as a rectangular window. The machine learning system for reconstructing masked regions can be trained from scratch using images taken from healthy patients. As discussed above, because a single input image can have multiple patches, the machine learning system can be trained to process multiple patches, or multiple machine learning systems can be utilized for the different patches. The reconstructed images, and the pre-proceed images (or the input images 500 if not pre-processed) are then compared to measure their similarity 508. The label and/or score are finally determined 510 based on the measured similarities 508. In other words, where the machine learning system is trained to reconstruct portions of the image based on images of normal and healthy eyes, a high level of similarity between the unmasked input or pre-processed images 500, 502 and the reconstructed image indicate that the masked portion is normal and healthy. In contrast, a low level of similarity indicates that input or pre-processed image 500, 502 is abnormal.

Figure 6:
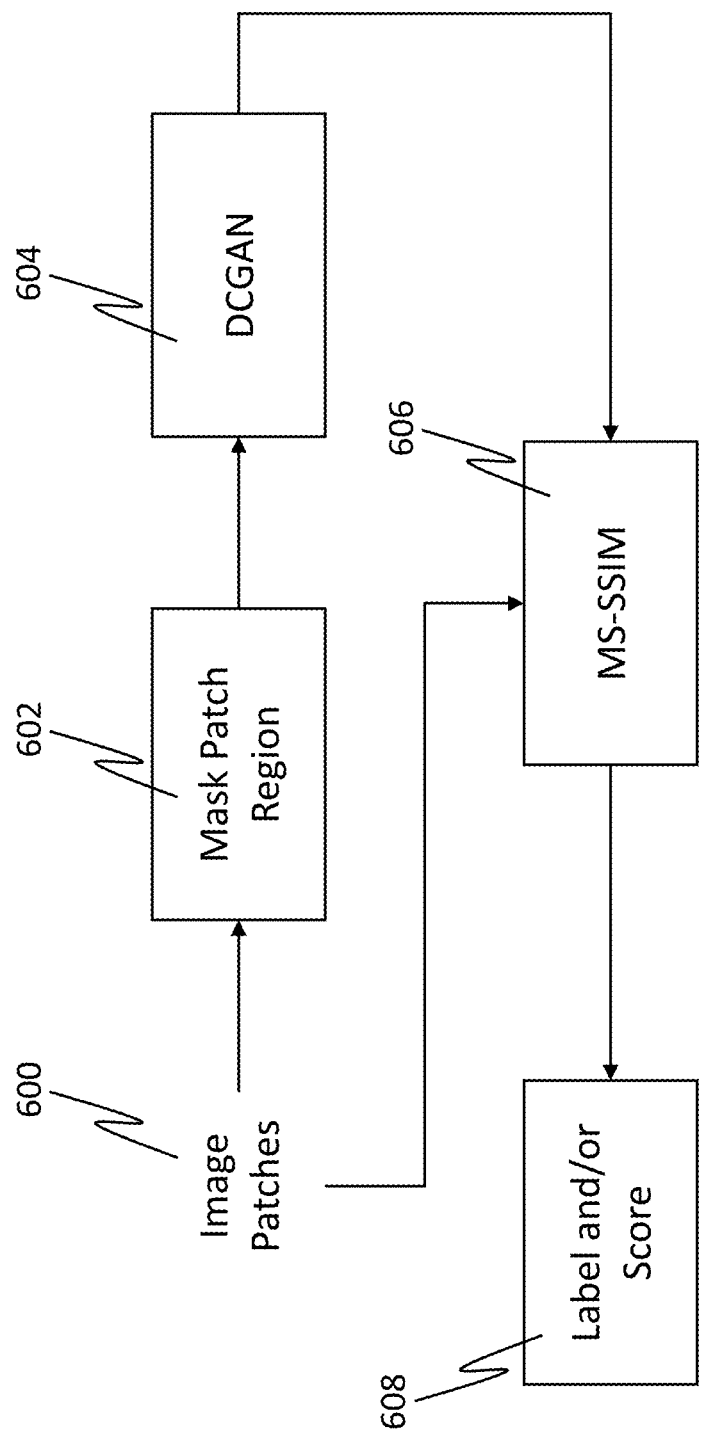
FIG. 6 illustrates another example image inpainting architecture of an anomaly detection screener system and method of the present disclosure.

A particular example of the image inpainting approach is illustrated in FIG. 6. Therein, the input images and/or the pre-processed input images are image patches 600. Regions of these patches are then masked 602 and reconstructed 604 by a DCGAN model. A DCGAN model comprises generator network that encodes and decodes an input image or patch, and discriminator network that determines whether an image or patch is generated (e.g., by a generator network) or is original to the image or patch. The discriminator network helps the generator network to realistically inpaint/reconstruct images. Following reconstruction 604, the reconstructed image patch is compared with original unmasked image patch using a multiscale structural similarity (MS-SSIM) 606 technique to make a similarity measurement 606. If a result of the MS-SSIM measurement is very small or close to zero (indicating little similarity), it can be determined that input image patch 600 represents some type of disease/anomaly. As noted above, this score can also imply the degree of severity or the type of the disease, and identify a label of "normal" or "abnormal" by setting threshold value for the similarity measure.

Figure 7:
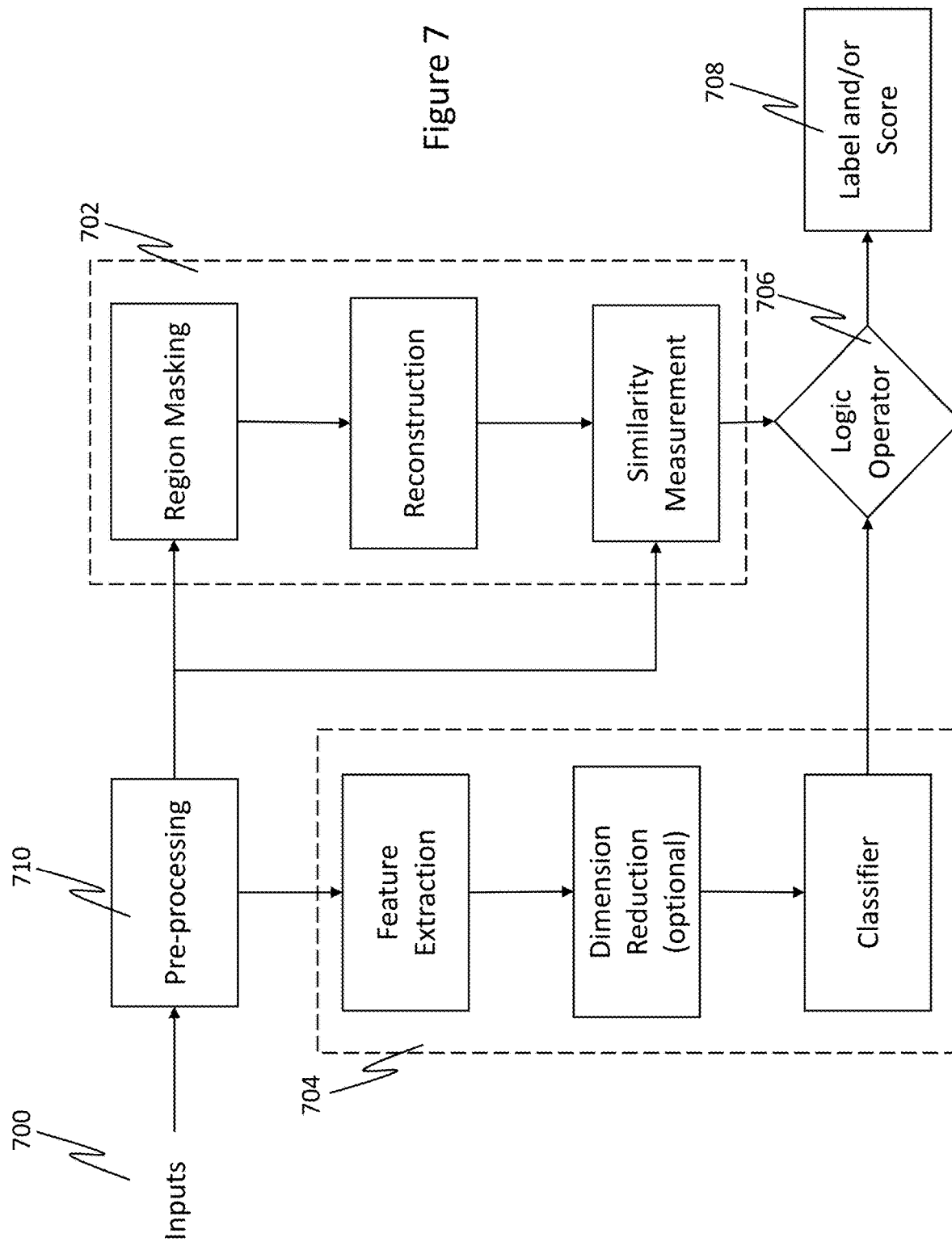
FIG. 7 illustrates an example ensemble anomaly detection architecture of an anomaly detection screener system and method of the present disclosure.

The third approach noted above, ensemble anomaly detection, utilizes both the classification and the inpainting approaches in a single system. In one example, each approach is executed in parallel on a common input to detect an anomaly. The final label and/or score then may be aggregate of the two approaches. For example, in some embodiments the final label may be 'abnormal' if either one or both approaches output a result that would be classified as abnormal (considered an 'or' combination); however, other embodiments may require that both approaches output a result of 'abnormal' for that to be used as the final label (considered an 'and' combination). An example of this approach is illustrated in FIG. 7, where a common input image 700 is input to both a classification system 702 and an inpainting system 704. The one class-classification system 702 and the inpainting system 704 may be of the type described above. The output of each system 702, 704, is then combined via a logical operator 706 to determine the label and/or score 708 of the input image 700. The logical operator 706 may be an OR operator for systems designed to output a label and/or score as an 'or' combination, or be an AND operator for systems designed to output a label and/or score as an 'and' combination, as described above.

While FIG. 7 illustrates that a common pre-processing 710 may be performed on the input image 700, as an alternative, different pre-processing may be performed for each system 702, 704. Of course, other masking, reconstruction, and similarity measurement techniques may be used and are considered within the scope of the present disclosure. Still further, although FIG. 7 illustrates the classification system 702 and the inpainting system 704 in parallel, it is also envisioned that these systems may be executed sequentially in any order.

It is also noted that multiple anomaly detections can be similarly executed in parallel for the same data, but with different resolutions, thereby forming a multi-resolution system. In other words, the above process may be performed multiple times on the same input data (e.g., from the same volume), however each iteration of the processes would use input images of different sizes/dimensions/resolutions. The process may also be performed on different inputs, thereby forming a multivariate system. In the above embodiments, the final output label and/or scores can be compiled from individual B-scan/image patch label/scores in a multi-resolution and multivariable form. With these embodiments, it is possible to identify multiple abnormalities (e.g., medical conditions) in a single patient. For example, some minor structural changes caused by abnormalities (e.g., drusen) may be most effectively identified by analyzing small-sized patches, whereas other abnormalities can be most effectively identified by analyzing larger-sized images. Similarly, different extracted features, or analysis of different physiological regions may be most indicative of different abnormalities.

The above architectures are flexible to accommodate a wide range of input types and can be applied to general disease anomaly detection. Besides the above mentioned traditional 3D scan-based B-scan input(s), the input can be customized towards glaucomatous feature associated images or measurements, for example, derived concentric circle or elliptical scans either around the disc or the fovea, or customized scans at optic nerve head or collections of non-raster scans (i.e., not traditional 3D scans) along nerve fiber bundles or various layer thickness measurement maps such as partial or full retinal nerve fiber layer thickness maps. The steps described herein, such as pre-processing, CNN model, DCGAN model, MS-SSIM and one class classifier, could be similar and applicable to all these situations. It should also be noted that these customizations may apply to pathologies other than glaucoma as well.

Figure 8:
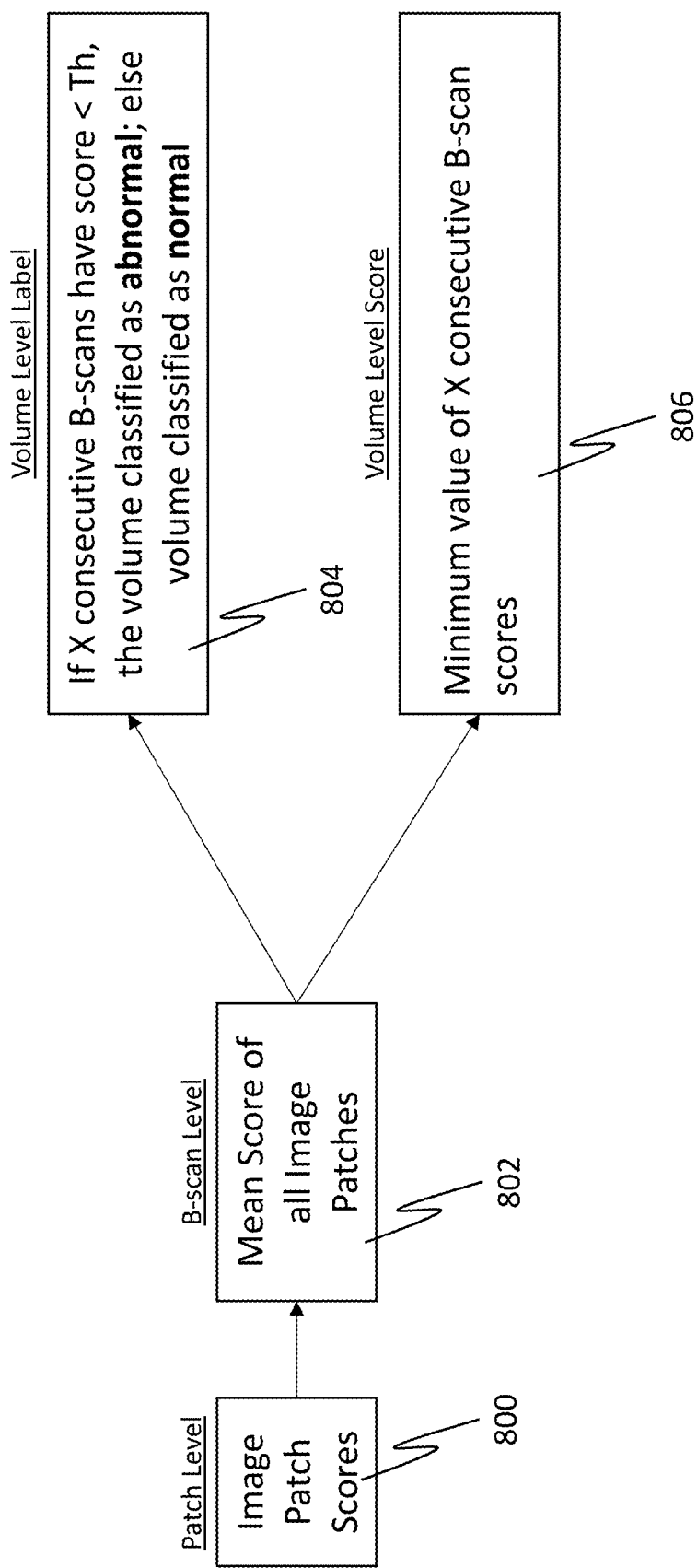
FIG. 8 illustrates an example of determining a volume label and/or score from individual image or image patch scores according to the system and method of the present disclosure.

FIG. 8 shows an example of how a volume label and/or score can be derived from individual image or image patch scores. Therein, each image or patch has a label and/or score 800 determined according to one of the above-described screener architectures, for example, the score being output by a classifier or a similarity measurement technique. A mean score 802 of these images is then determined, the mean score representing a "B-scan level" (or local) score. If there are then X consecutive (e.g., adjacent) B-scans having a score less than a predetermined threshold Th, the volume (or composite set of images) may be given an "abnormal" label 804. The X number of consecutive scans can be any number. For example, in one embodiment, the volume is labeled as abnormal if four or more consecutive B-scans have a score less than a zero threshold. Otherwise the volume is labelled "normal". The score for the volume (or composite set of images) 806 is then determined as the minimum value of any 4 consecutive B-scan scores. For example, if there are multiple sets of four consecutive B-scans having scores are less than zero, the smallest score among all of the sets may be considered the score for the volume. These volume scores 806 and labels 804 represent global scores and labels. Of course the above thresholds are not limiting, and any threshold criteria may be considered. Similarly, any statistical calculation(s) (for example, minimum, maximum, mean, median, standard deviations) may be used instead of those noted above. As noted above, in some embodiments the sign of the score may be reversed such that a negative value represents a normality, and a positive value represents an abnormality (thus the comparison for determining a label may be whether the score is greater than, rather than less than, the threshold). Similarly, the score may change in any manner with respect to severity. For example, the score may increase or decrease linearly or exponentially as severity changes.

Still further, the above-described process may be repeated for a common image or volume with a different feature extraction and/or classifier in order to make further pathological determinations. For example, a first iteration of the process may be used to determine whether a particular abnormality exists (e.g. a type of disease) and a further iteration may be used to determine the particular pathology of that type of disease that exists. In the former iteration, the machine learning system (e.g., including feature extraction CNN, the classifier, or the reconstructing model) may be particularly trained to recognize the abnormality, whereas in the latter iteration, the machine learning systems may be trained differently to recognize the particular pathologies.

As discussed above, an output of the system and method described herein may be a label and/or score of an input image(s) or other data set. Additional outputs can include any of the images resulting from the processing and pre-processing, and data accumulated during the processing and pre-processing. For example, outputs may include heat maps (or the corresponding data) indicating which regions of individual images or of image volumes that contributed most to a corresponding score and label determined by the system and method. These outputs may be provided directly to an end user, for example, via a display, or stored for later viewing and/or analysis.

Example Test

FIGS. 9-11 illustrate results of a test of the above-described methodology. In particular, the test used two independent data sets representing a normal eye, and one data set representing an eye with a retinal disease. Each set comprised 6 mm×6 mm 3D OCT volume data. The retinal disease symptoms included, among others, drusen, hard drusen, AMD, epiretinal membrane (ERM), macular edema, retinopathy, and central serous chorioretinopathy (CSC). As these figures merely represent one test, it is noted that different input conditions and types of pathologies, different scan regions (including those with anterior images) could be used.

Figure 9B:
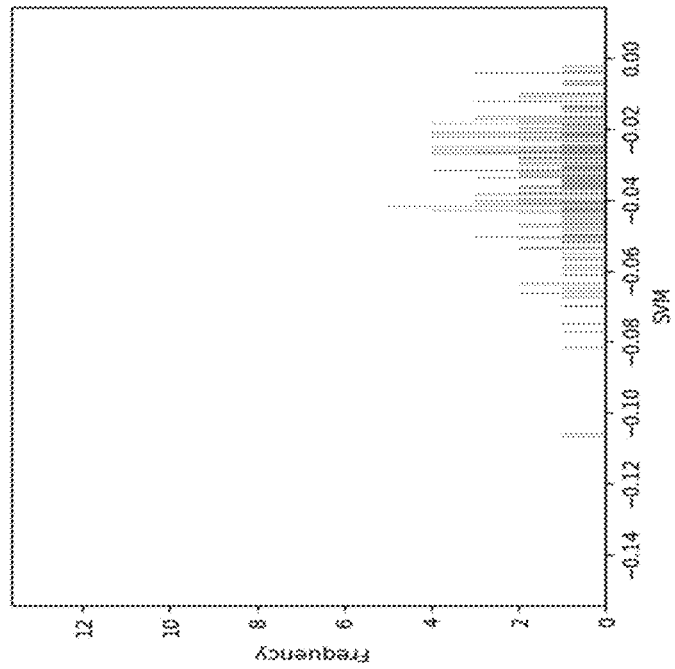
FIGS. 9A and 9B illustrate histograms of scores for two conditions detected during a test of the system and method of the present disclosure.
Figure 9A:
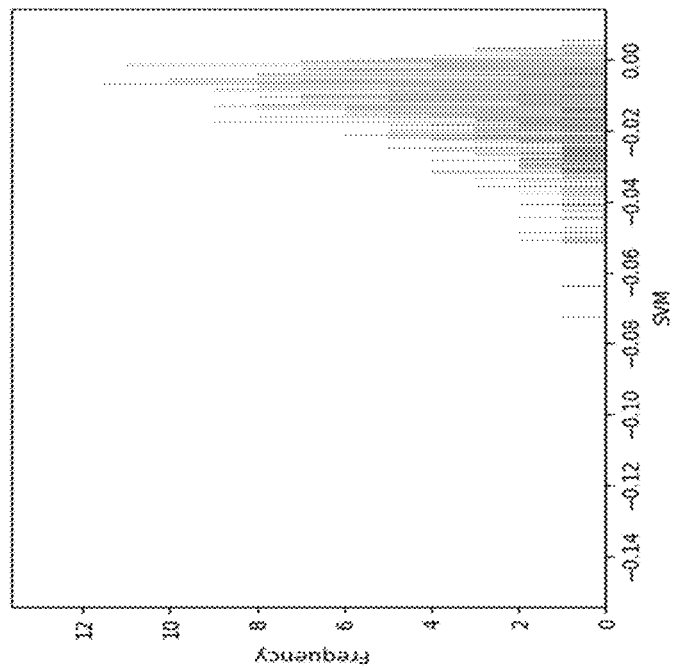

More particularly regarding FIG. 9, FIG. 9A illustrates a histogram showing the number of B-scans within the tested volume having a particular score indicative of drusen, as determined by a one class SVM classifier; and FIG. 9B illustrates a histogram for AMD scores. As seen therein, drusen was more prevalent—resulting in more B-scans being identified as showing drusen—and tended to present with scores less than −0.02, while AMD tended to produce stronger scores of about −0.02 to −0.04. As a precursor for AMD, the presence of drusen amounts to less severe structural changes and thus a lower score. This is consistent with the above discussion that drusen corresponds to lower scores than AMD, and that a threshold may be applied to differentiate drusen scores from AMD scores and thus differentiate diseases associated with an abnormal label. Such histograms can also be used to identify a level of severity for an entire volume of B-scans, for example, by identifying the most common score or a range of the greatest density of scores. Further, as noted above, the negative value of the scores can be used to label them as abnormal and a greater absolute value of the score indicates a greater severity of structural change, or a particular type of disease.

Figure 10B:
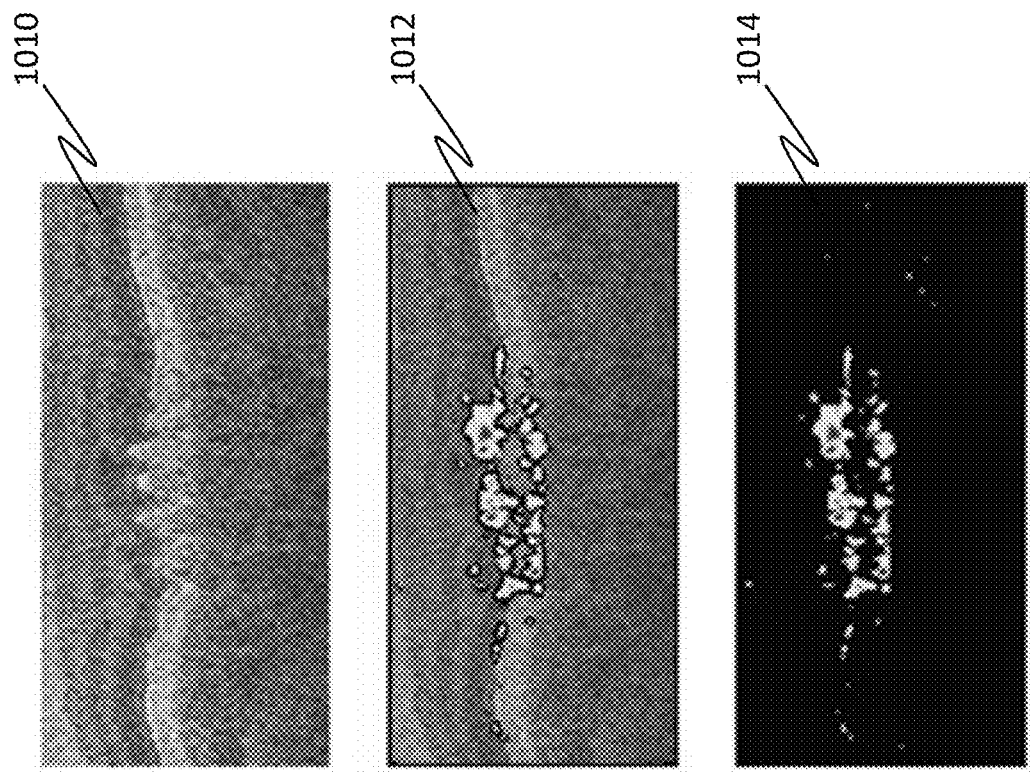
FIGS. 10A, 10B, and 10C B-scan images and corresponding heat maps for three different score values determined during a test of the system and method of the present disclosure.
Figure 10A:
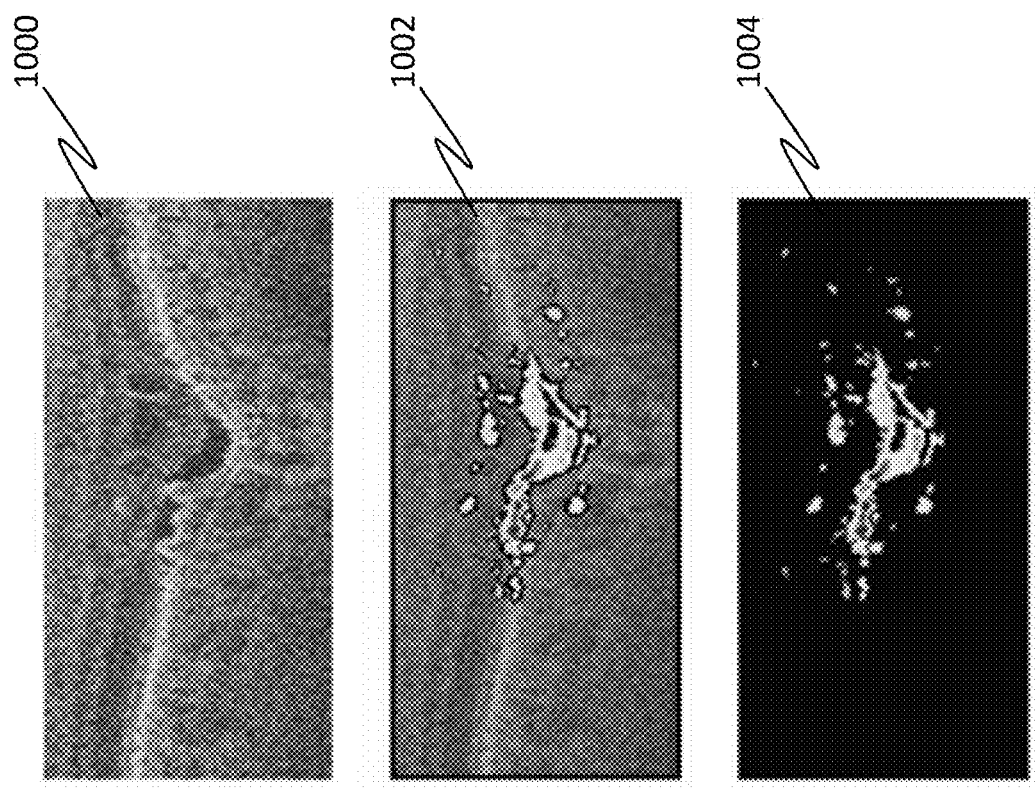
Figure 10C:
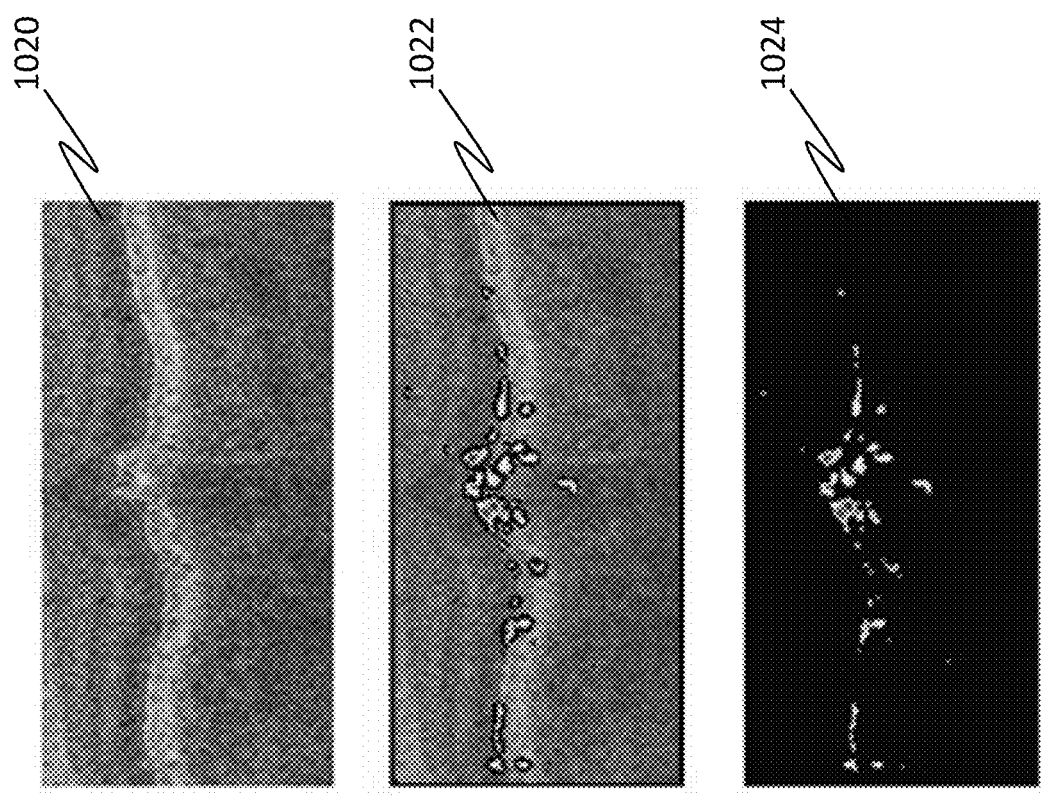

FIGS. 10A-10C illustrate three example B-scans from this test. FIG. 10A shows a B-scan 1000 having a score of −0.033461623, showing AMD in the image. FIG. 10B shows a B-scan 1010 with drusen and having a score of −0.022405657. FIG. 10C shows a B-scan 1020 also with drusen, but having a lower score of −0.01064716. The middle panels of each of FIGS. 10A-10C illustrate the B-scans overlaid with heat maps 1002, 1012, 1022; and the bottom panels illustrate the heat maps 1004, 1014, 1024 by themselves. The heat maps indicate areas of each B-scan contributing the most to the final classification. These heat maps may also be produced in color, to show degrees of contribution (e.g., blue indicating little or no contribution to red indicating the most contribution).

Finally, FIG. 11 illustrates an ROC analysis for the test based on scoring and labeling at the volume level. ROC analyses can be used for evaluating the quality or performance of tests. For example, an ROC curve is a graphical plot that illustrates the diagnostic ability of a binary classifier system as its discrimination threshold is varied. The ROC curve may be created by plotting a true positive rate (TPR) against the false positive rate (FPR) at various threshold settings. The area under the curve (often referred to as simply the AUC) represents an index of diagnostic ability. The larger the AUC, the better quality and performance of the system. The sensitivity at any point on the curve can be identified as the true positive rate, and the specificity at any point on the curve can be identified as one minus the false positive rate.

Figure 11A:
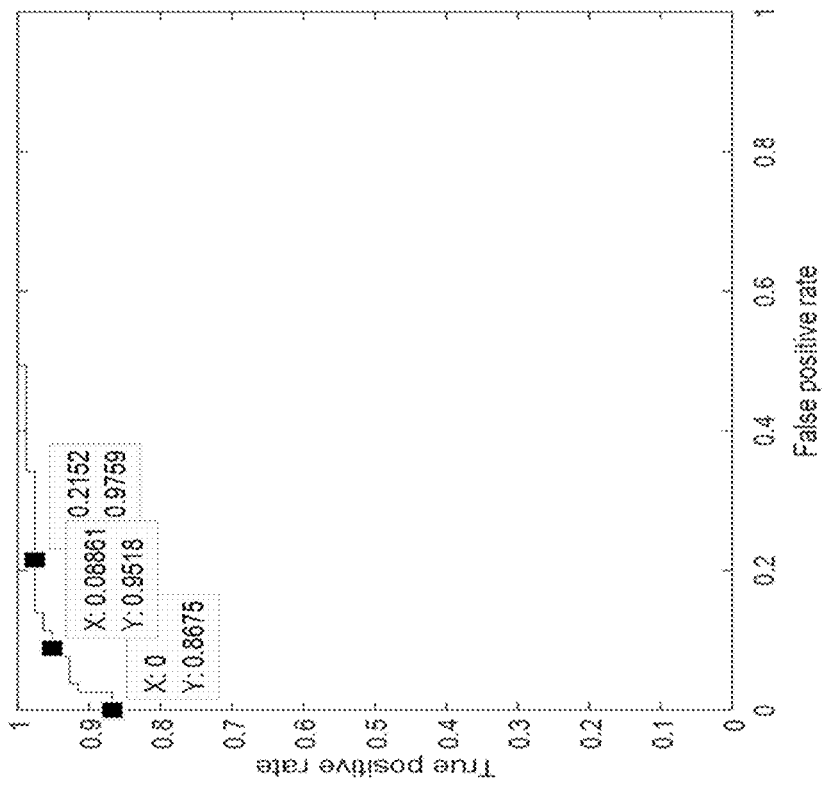
FIGS. 11A and 11B illustrate a receiver operating characteristic (ROC) analyses for a test of the system and method of the present disclosure.
Figure 11B:
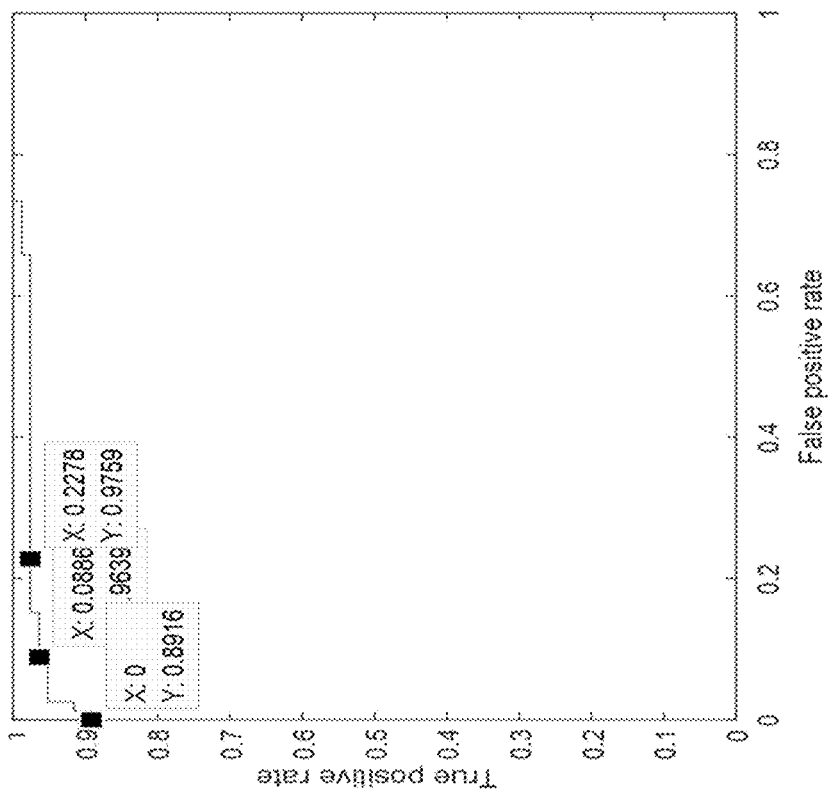

In particular, FIG. 11A shows an ROC curve where the score for the volume was based on a sum of four consecutive individual B-scan scores. FIG. 11B shows an ROC curve where the score for the volume was based on a mean of all available individual B-scan scores. For these analyses, a positive identification was an identification of a retinal disease by the system and method. For the analysis in FIG. 11A, the system exhibited a sensitivity of 0.8916 for a specificity of 1, and reached a sensitivity of 0.9759 at a specificity of 0.7722. This corresponds to an area under the ROC curve of 0.9791. FIG. 11B, for a mean calculation to determine a volumetric score, showed a sensitivity of 0.8675 for a specificity of 1 and reached a sensitivity of 9.9759 at a specificity of 0.7848. The area under the curve for FIG. 11B was thus 0.9834.

As suggested above, a system for executing the above-described method is also contemplated within the scope of the present disclosure. Such a system may include a computer having one or more processors (e.g., in the form of an integrated circuit(s), discrete circuitry, or the like) for executing the method, storage (such as a hard disk, memory, RAM, or the like) and an input/output interface (e.g., display, keyboard, mouse, and the like). The storage may be located locally with the computer, or remotely, for example at a centralized database. The system may also be integrated or separate from a system used to capture the images and other input data. For example, the computer may be the same as that used to control an optical coherence tomography system.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What we claim is:

1. An image processing method comprising:
receiving a first image of an object;
extracting, with a trained machine learning system, a feature of the first image or of a physiological structure shown in the first image, the first image being an input to the trained machine learning system;
classifying, with a first trained classifier, the first image based on the extracted feature, the extracted feature being an input to the first trained classifier;
determining a label and/or score of the first image based on the classification of the first image;
receiving a second image of the object;
extracting, with the trained machine learning system, a feature of the second image or of a physiological structure shown in the second image, the second image being an input to the trained machine learning system;
classifying, with a second trained classifier, the second image based on the extracted feature of the second image, the extracted feature of the second image being an input to the second trained classifier and the second classifier being trained differently than the first classifier;
determining a label and/or score of the second image based on the classification of the second image;
determining a composite label by comparing scores of a first predetermined number of images to a predetermined threshold; and
determining a composite score by performing a statistical calculation on a second predetermined number of images,
wherein the first image and the second image are image patches,
wherein the second image is of a different type, location, size, and/or resolution than the first image, and
wherein the first predetermined number of images includes at least the first image and the second image, and the second predetermined number of images includes at least the first image and the second image.

2. The image processing method of claim 1, wherein the image patches are from a common cross-sectional image of the object.

3. The image processing method of claim 1, wherein:
the first trained classifier is trained with normative images corresponding to a region of the first image that includes the extracted feature of the first image, and
the second trained classifier is trained with nonnative images corresponding to a region of the second image that includes the extracted feature of the second image.

4. The image processing method of claim 1, wherein the first image and the second image comprise at least some of the same data.

5. The image processing method of claim 1, wherein the first image and the second image are from a common 3D volume.

6. The image processing method of claim 1, wherein the first image and the second image do not comprise any of the same data.

7. The image processing method of claim 1, wherein the first image and the second image have a different size or a different resolution.

8. The image processing method of claim 1, wherein the first image and the second image are from different 3D volumes.

9. An image processing method comprising:
receiving a first image of an object
extracting, with a trained machine learning system, a feature of the first image or of a physiological structure shown in the first image, the first image being an input to the trained machine learning system;
classifying, with a first trained classifier, the first image based on the extracted feature, the extracted feature being an input to the first trained classifier;
determining a label and/or score of the first image based on the classification;
receiving a second image of the object;
extracting, with the trained machine learning system, a feature of the second image or of a physiological structure shown in the second image, the second image being an input to the trained machine learning system;
classifying, with a second trained classifier, the second image based on the extracted feature of the second image, the extracted feature of the second image being an input to the second trained classifier and the second classifier being trained differently than the first classifier; and
determining a label and/or score of the second image based on the classification,
wherein the first image and the second image are image patches,
wherein the second image is of a different type, location, size, and/or resolution than the first image,
wherein the first image and the second image are from distinct spatial regions of a common cross-sectional image of the object, and
wherein the first trained classifier and the second trained classifier are component classifiers of an ensemble classifier, the first trained classifier being trained with training image patches from the distinct spatial region corresponding to the first image, and the second trained classifier being trained with training image patches from the different distinct spatial region corresponding to the second image.

10. The image processing method of claim 1,
wherein the composite label represents an abnormality when a first set of consecutive images of the first predetermined number of images have a score less than a threshold, and
wherein the composite score is a minimum score of a second set of consecutive images of the second predetermined number of images.

11. The image processing method of claim 1, further comprising:
determining an average of the score of the first image and the second image.

12. The image processing method of claim 1, wherein the first image is a B-scan or a cross-sectional image that includes a depth dimension.

13. The image processing method of claim 1, wherein the first image is an optical coherence tomography image.

14. The image processing method of claim 1, wherein the label of the first image or of the second image identifies whether the object is normal or abnormal, and the score of the first image or of the second image indicates a degree of the normality or abnormality, or indicates a type of the abnormality.

15. The image processing method of claim 1, wherein the first trained classifier is a binary classifier.

16. The image processing method of claim 1, wherein the first trained classifier is a deep learning model.

17. The image processing method of claim 1, wherein the first trained classifier is trained with only normative data.

18. The image processing method of claim 1, wherein the first trained classifier is a one-class support vector machine.

19. The image processing method of claim 1, wherein the trained machine learning system is a convolutional neural network.

20. The image processing method of claim 1, wherein the object is an ophthalmological structure.

21. The image processing method of claim 9, further comprising:
   determining a composite label or a composite score based on the label or the score of the first image and based on the label or the score of the second image.

22. An image processing method comprising:
   receiving a first image of an object;
   extracting, with a first trained machine learning system, a feature of the first image or of a physiological structure shown in the first image, the first image being an input the first trained machine learning system;
   classifying, with a first trained classifier, the first image based on the extracted feature, the extracted feature being an input to the first trained classifier;
   masking a region of the first image;
   reconstructing, with a second trained machine learning system, the region of the first image;
   determining a similarity between the reconstructed region of the first image and a corresponding region of the first image as received; and
   determining a label and/or score of the first image based on the classification and the determined similarity.

* * * * *